(12) United States Patent
Grosser

(10) Patent No.: US 10,335,552 B2
(45) Date of Patent: Jul. 2, 2019

(54) PIERCING MEANS PROTECTIVE DEVICE FOR A SYRINGE

(71) Applicant: Gerresheimer Regensburg GmbH, Regensburg (DE)

(72) Inventor: Jörg Grosser, Lappersdorf (DE)

(73) Assignee: Gerresheimer Regensburg GMBH, Regensburg (DE)

( * ) Notice: Subject to any disclaimer, the term of this patent is extended or adjusted under 35 U.S.C. 154(b) by 99 days.

(21) Appl. No.: 15/593,049

(22) Filed: May 11, 2017

(65) Prior Publication Data
US 2017/0326306 A1    Nov. 16, 2017

(30) Foreign Application Priority Data

May 13, 2016   (DE) .......................... 10 2016 108 870

(51) Int. Cl.
*A61M 5/32*     (2006.01)
*A61M 5/31*     (2006.01)

(52) U.S. Cl.
CPC ... *A61M 5/3202* (2013.01); *A61M 2005/3109* (2013.01)

(58) Field of Classification Search
CPC .................................................. A61M 5/3202
See application file for complete search history.

(56) References Cited

U.S. PATENT DOCUMENTS

| 4,636,201 | A  | 1/1987 | Ambrose et al. |
| 5,147,325 | A  | 9/1992 | Mitchell et al. |
| 6,719,732 | B2 | 4/2004 | Courteix |

| 2013/0261562 | A1* | 10/2013 | Fabian ............... A61M 5/3202 604/263 |
| 2015/0335830 | A1* | 11/2015 | Horita ................ A61M 5/3204 604/192 |
| 2016/0106929 | A1 | 4/2016 | Fournier et al. |

FOREIGN PATENT DOCUMENTS

| DE | 3685567  | 1/1993 |
| DE | 60110728 | 5/2006 |

OTHER PUBLICATIONS

European Supplemental Search Report, dated Oct. 18, 2017, corresponding to European Application No. 16178695.9, a related application, 3 pp.
German Office Action, dated Jan. 9, 2017, in corresponding German Patent Application No. 10 2016 108870.6, 3 pp.

* cited by examiner

*Primary Examiner* — Nathan R Price
*Assistant Examiner* — Melissa A Snyder
(74) *Attorney, Agent, or Firm* — Leydig, Voit & Mayer, Ltd.

(57) ABSTRACT

The invention relates to a piercing means protective device for a syringe having a syringe body and a piercing means arranged at the distal end of the syringe body, comprising a dimensionally stable sleeve element, which extends along an axial direction and at least partially encloses an inner element extending along an axial direction, wherein the inner element consists of a resilient material and at least partially encloses the piercing means. The piercing means protective device is characterized in that a connection element connected to the sleeve element has at least one projection extending in an axial direction, which projection is received at least in portions in a recess of the inner element, so that a connection with a force fit and/or an interlocking fit exists between the sleeve element and the inner element.

15 Claims, 10 Drawing Sheets

PIERCING MEANS PROTECTIVE DEVICE FOR A SYRINGE

CROSS-REFERENCE TO RELATED APPLICATIONS

This application is a U.S. Nonprovisional Application filed under 35 U.S.C. § 111(a) which claims the benefit of German Application No. 10 2016 108 870.6, filed May 13, 2016. This application is hereby incorporated by reference in its entirety.

BACKGROUND OF INVENTION

The invention relates to a piercing means protective device for a syringe having a syringe body and a piercing means arranged at the distal end of the syringe body, comprising a dimensionally stable sleeve element, which extends along an axial direction and at least partially encloses an inner element extending along an axial direction, wherein the inner element consists of a resilient material and at least partially encloses the piercing means.

Piercing means protective devices of this kind are normally used on prefilled syringes. The handling of such syringes is very simple, as the medium does not have to be transferred to the syringe prior to application. For vaccines and countless other medicines they are now the first-choice primary packaging material. These syringes are usually manufactured from glass or plastics material (for example COC, COP) and are equipped with a piercing means. Such piercing means, for example cannulas, normally have a very finely polished portion to permit an injection that is as pain-free as possible. Polished portions of this kind can easily be damaged by mechanical influences, as a result of which the patient may be caused unnecessary pain during an injection. The piercing means are therefore provided with a protective cap made of a resilient material. Such a flexible needle shield (FNS) protects the finely polished portion of the piercing means from mechanical influences due to its resilient properties. Furthermore, the sterility of the piercing means should be ensured. To this end, the FNS also encompasses the conical end piece of the syringe body. The piercing means is hermetically sealed by the seat of the inner element on the end piece of the syringe body, thereby ensuring the sterility of the piercing means.

However, due to its resilient properties, an FNS of this kind does not offer adequate protection from greater mechanical loads. Dimensionally stable sleeve elements were accordingly already arranged on the FNS. Such a system, consisting of a dimensionally stable sleeve element and a flexible needle shield (FNS), is also termed a rigid needle shield (RNS). The connection between the FNS and the RNS poses a problem here. In conventional piercing means protective devices, the FNS is held in a receptacle of the sleeve element. The resilient element frequently slips out of the receptacle and as result becomes separated from the dimensionally stable sleeve element. The dimensionally stable sleeve element could be lost in this case, giving rise to the risk of the piercing means being damaged. In addition, without any enclosing stable component, the FNS may be punctured and thus poses a risk in respect of needlestick injuries to the user.

SUMMARY OF THE INVENTION

The object of the present invention accordingly is to provide a piercing means protective device which avoids the disadvantages mentioned at the outset and which is constructively simple and inexpensive to manufacture. Furthermore, the object of the invention is to provide a syringe which is equipped with such a piercing means protective device.

These objects are achieved by a piercing means protective device for a syringe having a syringe body and a piercing means arranged at the distal end of the syringe body, comprising a dimensionally stable sleeve element, which extends along an axial direction (X) and at least partially encloses an inner element extending along an axial direction (X), wherein the inner element consists of a resilient material and at least partially encloses the piercing means. The piercing means protective device is characterised in that a connection element connected to the sleeve element has at least one projection extending in an axial direction (X), which projection is taken up at least in portions in a recess of the inner element, so that a connection with a force fit and/or an interlocking fit exists between the sleeve element and the inner element.

The dimensionally stable sleeve element constitutes an adequate protection for the piercing means in respect of mechanical loads. Furthermore, the removal of the piercing means protective device is made easier, as the user can grip the piercing means protective device better. It is further ensured by the connection element that a mechanically fixed connection exists between the inner element and the sleeve element. An undesirable slipping of the inner element out of the sleeve element is thus effectively suppressed.

The piercing means, in particular the polished portion of the piercing means, is protected from mechanical influences and damage by the inner element. The piercing means may be a cannula, a needle or a lancet, for example.

The syringe body is preferably configured as a hollow circular cylinder and has in its distal end region a conical end piece on which the piercing means is arranged.

The distal end of the syringe is closest to the application site. The piercing means is thus arranged at the distal end. The actuation elements, for example the plunger, are normally arranged at the proximal end. The terms "distal" and "proximal" are to be understood by analogy for the piercing means protective device. The axial direction (X) is further subdivided into a distal direction ($X_1$) and a proximal direction ($X_2$). A radial direction (R) runs perpendicular to the axial direction (X).

The syringe body preferably consists of glass or a polymer material, preferably a polyolefin, for example polypropylene or polyethylene, particularly preferably of a cyclic olefin polymer (COP) or of a cyclic olefin copolymer (COC).

The inner element is preferably configured substantially cylindrically. Particularly preferably, the inner element has a substantially circular base area. At its proximal end, the inner element advantageously has another recess on which the piercing means of the syringe can be arranged. The other recess preferably has a first portion, which has a constant inner diameter and in which a distal end piece of the syringe body can be received. It is also preferable that the other recess has a second portion which has an inner diameter that decreases in an axial direction (X).

The inner element advantageously abuts the distal end region of the syringe body in a sealing manner or the inner element is arranged partially over the distal end region and/or the conical end piece of the syringe body. The piercing means is thus hermetically sealed and protected from contamination. The sterility of the piercing means is accordingly ensured.

According to a particularly preferred embodiment, the sleeve element is formed substantially as a circular hollow cylinder and has a distal and a proximal end. The hollow cylinder preferably has a closed wall. However, it would also be conceivable for the wall to have slots or recesses. The sleeve element could therefore also have a finned wall. The connection element is preferably arranged at the distal end of the sleeve element. The connection between the sleeve element and the connection element is preferably a connection with a force fit and/or an interlocking fit and/or is a material-uniting connection. Such a connection with an interlocking fit could be a clip-on connection or a tongue and groove connection, for example. A possible material-uniting connection could be an adhesive or welded connection, for example. A possible connection with a force fit could be a screw connection or a frictional connection, for example.

At its distal end, the inner element preferably has a flange element extending in a radial direction (R) which is received in a receiving means of the sleeve element. The receiving means is advantageously arranged on the distal end of the sleeve element. The receiving means and the sleeve element are preferably formed integrally. However, it would also be conceivable for the receiving means to be a separate component and be connected to the sleeve element. Such a connection could be a clip-on connection, an adhesive connection or a welded connection.

The receiving means advantageously also has a first wall which extends in an axial direction (X) starting from the distal end of the sleeve element, and a second wall which extends substantially in a radial direction. The flange element rests preferably on the second wall of the receiving means, as a result of which the inner element is held in an axial direction or a distal direction during removal of the piercing means protective device in particular. The flange element preferably completely surrounds the inner element. However, it would also be conceivable for the flange element to be arranged only in portions on the outer surface of the inner element. It is further preferred that the receiving means is formed in the manner of a cylinder and thus has a closed first wall. However, it would also be conceivable for the first wall to have recesses or slots.

According to another preferred embodiment, the connection element has a circular base element on which the projection (9) is arranged. The circular base element preferably has a radial outer surface which is connected to the sleeve element. Due to the advantageous arrangement of the connection element on the distal end of the sleeve element, the connection element closes off the sleeve element at the distal end. The connection element is also a type of cover element. Thus the inner element is fixed in an axial or distal direction on the one hand, and a protection is provided against mechanical influences in this direction on the other hand.

According to a particularly preferred embodiment, the projection is arranged on the connection element centrally with respect to a central axis ($M_H$) of the sleeve element. The recess is preferably arranged centrally with respect to a central axis ($M_{IE}$) of the inner element. Due to the respective central arrangement and the connection between the connection element and the inner element, the inner element can advantageously be centred with respect to the sleeve element. The piercing means is thus arranged centrally in the inner element and is thus exposed to no mechanical loads in a radial direction.

Advantageously, the projection of the connection element is formed conically. The projection preferably tapers in this case starting from the circular base element in an axial direction (X). The projection is formed particularly preferably as a conical hollow cylinder. An outer diameter of a first region of the projection is preferably greater than an inner diameter of the recess of the inner element. The inner element is preferably resiliently deformed when the projection is received in the recess of the inner element. The flange element of the inner element is advantageously pressed by this deformation in a radial direction (R) onto the receiving means. The flange element of the inner element is preferably pressed by this deformation in a radial direction (R) onto the first wall of the receiving means. The inner element is prevented from slipping out in a proximal direction in a simple manner by this embodiment. On the one hand, a connection with a force fit and/or an interlocking fit exists between the projection of the connection element and the recess of the inner element. On the other hand, the flange element is pressed against the first wall of the receiving means, as a result of which a force fit exists between the flange element and the first wall of the inner element. Furthermore, a front face of the second wall is pressed against a portion of the inner element which lies below the flange element in a proximal direction. The flange element is thus effectively prevented from slipping over the second wall.

According to a preferred embodiment, at least one axial tolerance-compensation element is arranged on the base element of the connection element and extends in an axial direction (X) towards the inner element and contacts the inner element. The at least one axial tolerance-compensation element can therefore deform/compress the resilient inner element selectively or even penetrate said inner element. Thus constructional tolerances of the inner element, the sleeve element and the end piece of the syringe body are effectively compensated. Furthermore, the tolerance-compensation element additionally constitutes a fixing in an axial and a radial direction for the inner element.

At least two axial tolerance-compensation elements are preferably arranged on the base element of the connection element. It is particularly preferable if six axial tolerance-compensation elements are arranged on the base element of the connection element. The at least two or six axial tolerance-compensation elements are advantageously arranged in a circular manner around the projection. These tolerance-compensation elements are advantageously configured as cone-shaped projections or mandrels.

According to another advantageous embodiment, the axial tolerance-compensation element is configured as an annular element surrounding the projection. The annular element preferably tapers in an axial direction (X) towards the inner element. The annular element thus has a wide base area arranged on the circular base element and a narrow edge, which lies centrally over the base area and deforms/compresses or penetrates the inner element.

According to another embodiment, the projection comprises an outer surface on which ribs running in an axial direction are arranged. These ribs can deform/compress or penetrate the resilient material of the inner element. A more stable connection can thus be realized between the inner element and the connection element.

The resilient inner element preferably consists of rubber or a resilient synthetic elastomer. The sleeve element and the connection element preferably consist of a thermoplastic material. These elements are preferably manufactured by means of a single-component or multicomponent injection moulding process. The elements can thus be manufactured inexpensively with just one tool and in one operation.

According to another advantageous embodiment, the sleeve element is equipped with a surface which is slip-resistant and/or improves the haptic. This can be achieved for example by a coating or by a rubber coating. Gripping elements, such as projections or recesses, could also be provided.

The object is also achieved by a syringe, in particular a prefilled syringe, equipped with a piercing means protective device according to any of the preceding embodiments.

The syringe body is preferably configured as a hollow circular cylinder in which a piston is arranged movably. In its distal end region, the syringe preferably has a conical end piece on which the piercing means is arranged. The syringe body preferably consists of glass or a polymer, preferably a polyolefin, for example polypropylene or polyethylene, particularly preferably of a cyclic olefin polymer (COP) or of a cyclic olefin copolymer (COC).

Other advantages, aims and properties of the present invention are explained with reference to the following description of the attached drawings. Similar components can have the same reference signs in the various embodiments.

DETAILED DESCRIPTION OF THE INVENTION

Figure 1:
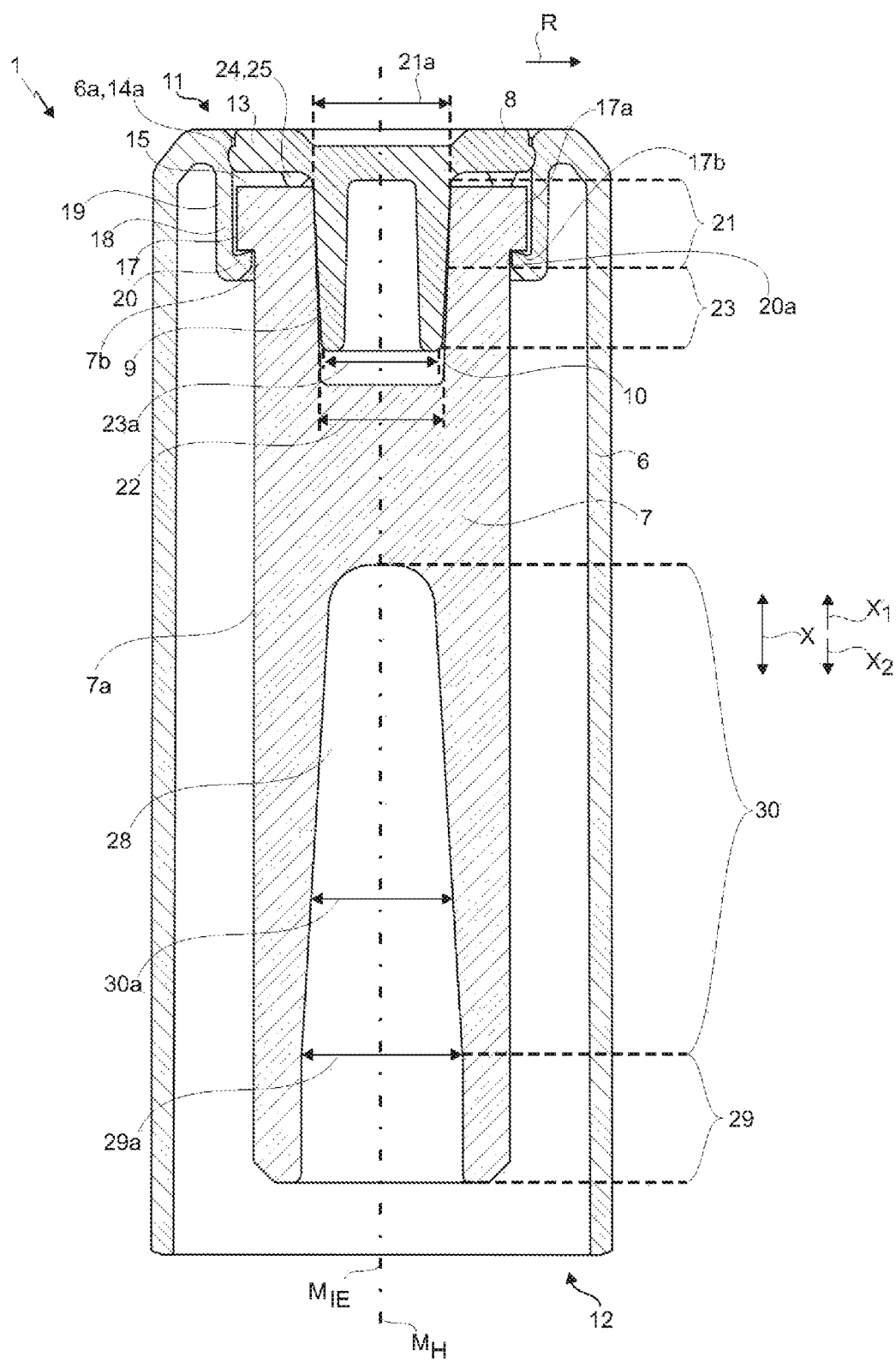
FIG. 1 is a sectional view of a piercing means protective device.

FIG. 1 shows a piercing means protective device (1) for a syringe (2) having a syringe body (3) and a piercing means (5) arranged at the distal end (4) of the syringe body (3), comprising a dimensionally stable sleeve element (6), which extends along an axial direction (X) and at least partially encloses an inner element (7) extending along an axial direction (X), wherein the inner element (7) consists of a resilient material and at least partially encloses the piercing means (3), wherein a connection element (8) connected to the sleeve element (6) has at least one projection (9) extending in an axial direction (X), which projection is received at least in portions in a recess (10) of the inner element (7), so that a connection with a force fit and/or an interlocking fit exists between the sleeve element (6) and the inner element (7).

Figure 10:
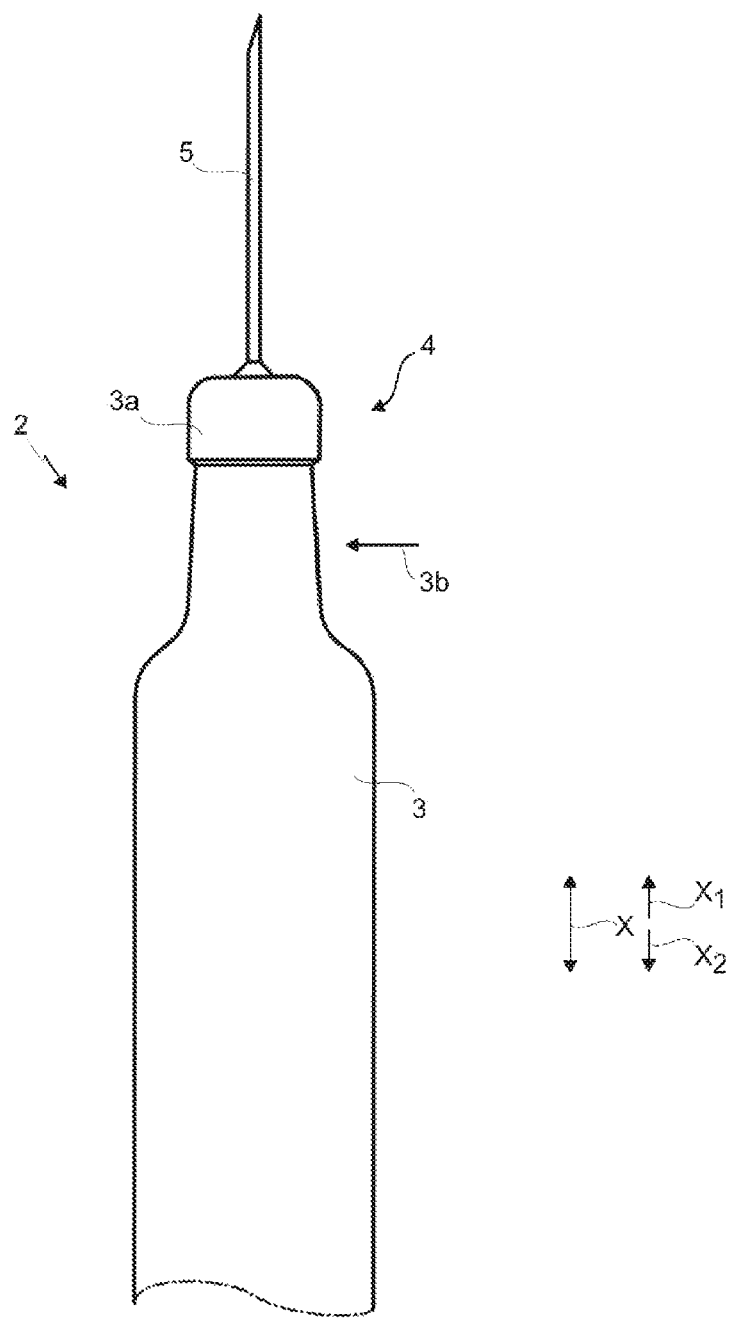
FIG. 10 is a side view of a syringe.

A typical syringe which can be provided with a piercing means protective device is shown in FIG. 10. The syringe (2) comprises a syringe body (3) configured as a hollow circular cylinder. The syringe body has a distal end region (3b) with a distal end (4). Arranged at the distal end (4) is a piercing means (5). This piercing means (5) is connected via a bore in the distal end region (3b) to the cavity of the syringe body (3), so that the medium to be injected during application of the syringe (2) can emerge from the cavity through the piercing means (5). The distal end region (3b) is configured as a conical end piece which has a smaller outer diameter than the syringe body (3). The syringe also has a transition region in which the outer diameter of the syringe body (3) merges into the outer diameter of the end piece.

Figure 7:
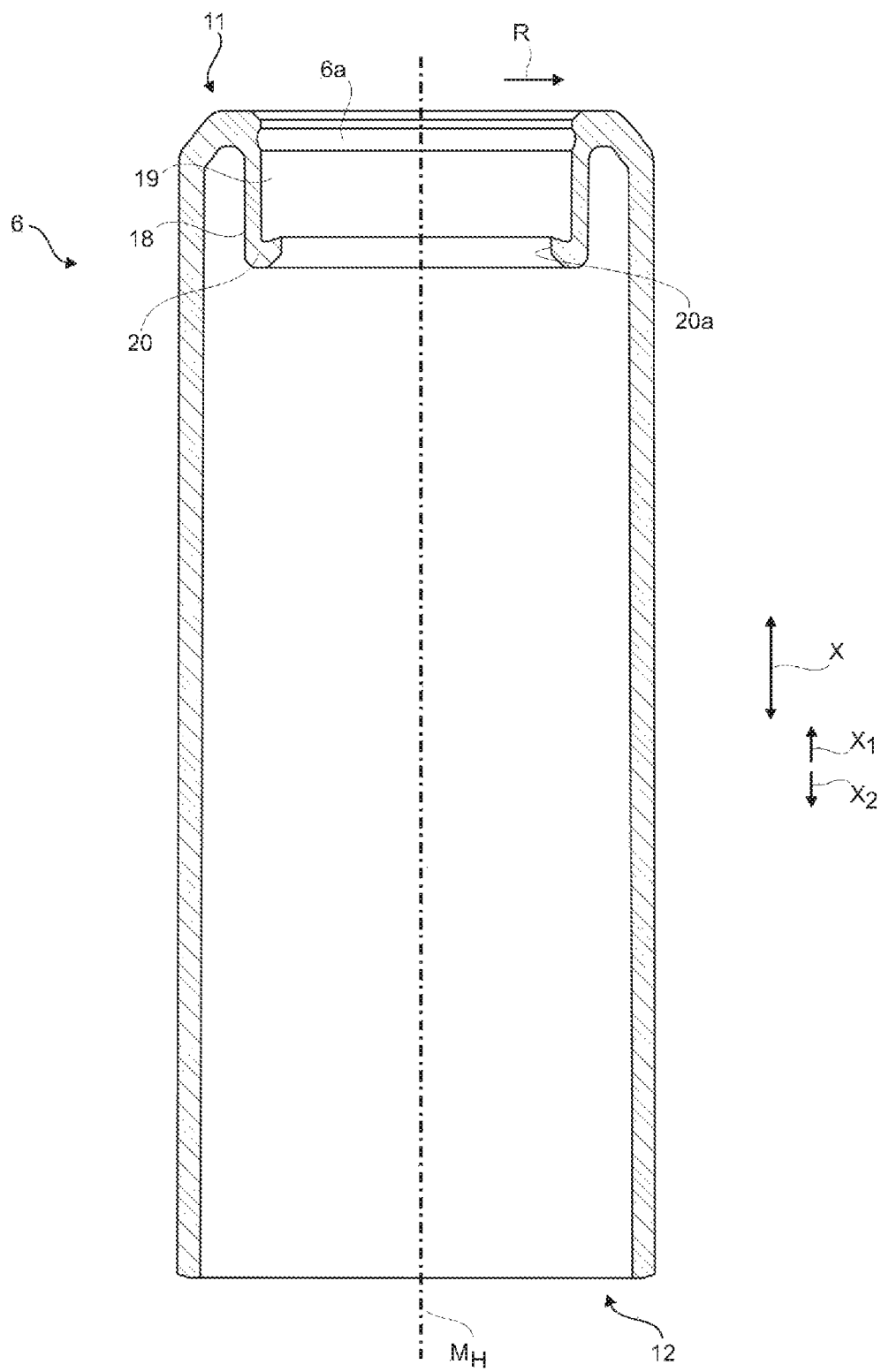
FIG. 7 is a sectional view of the sleeve element.
Figure 8:
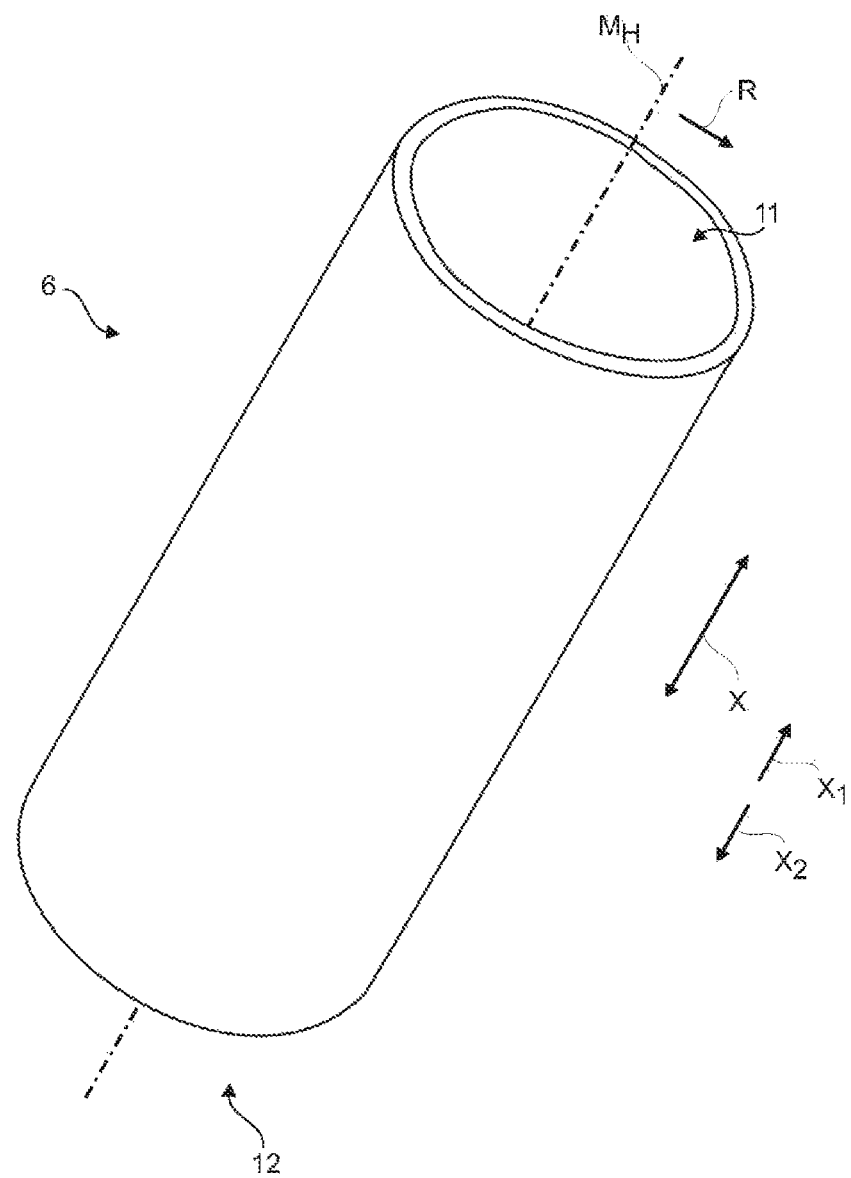
FIG. 8 is a perspective view of the sleeve element.
Figure 9:
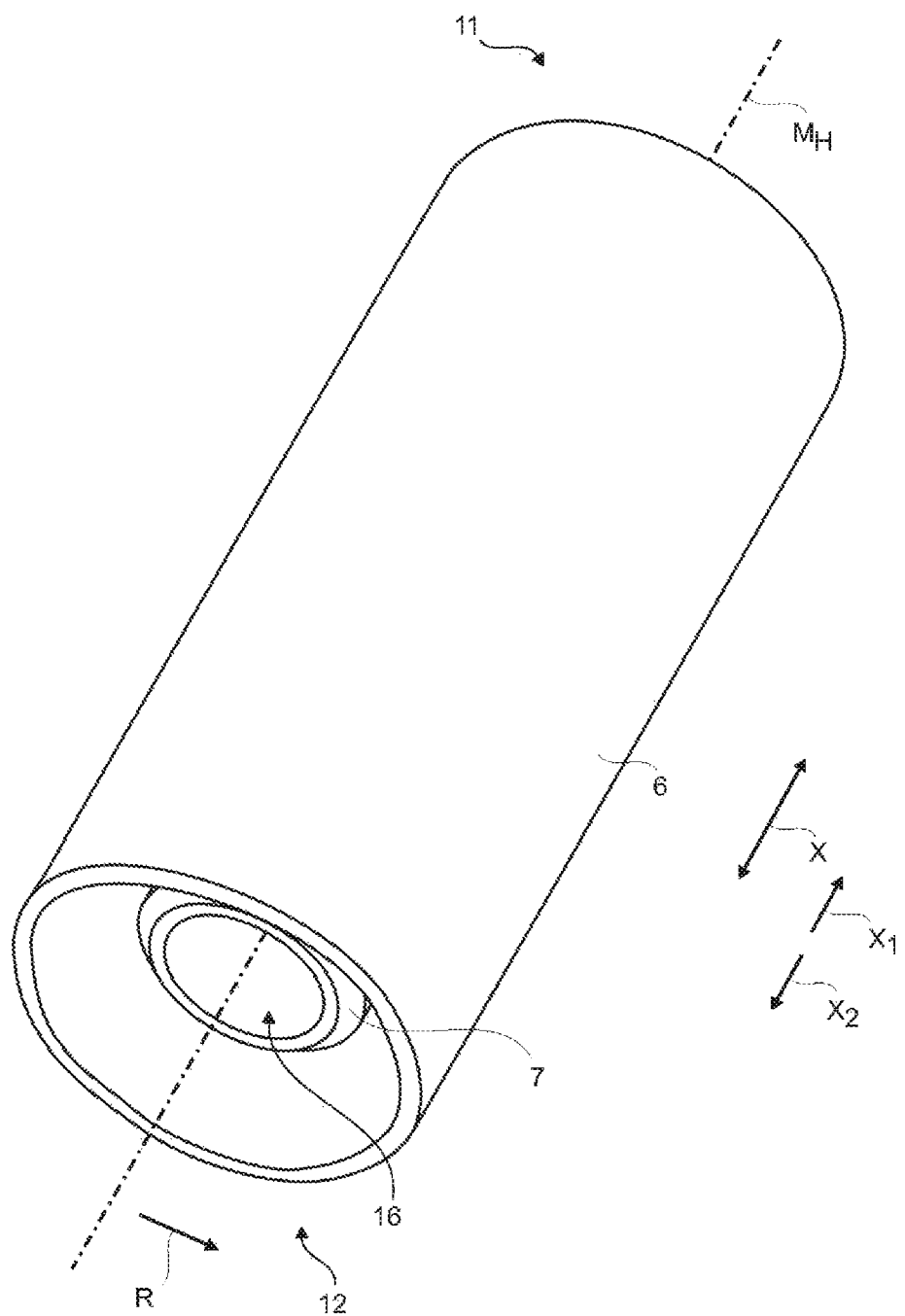
FIG. 9 is another perspective view of the sleeve element.

The sleeve element (6) is formed as a circular hollow cylinder and has a distal (11) and a proximal (12) end. This can be seen in FIGS. 1, 7, 8 and 9. FIG. 1 is a sectional view of the piercing means protective device (1) with the sleeve element (6), the inner element (7) and the connection element (8). In FIG. 7, only the sleeve element (6) is shown in a sectional view. In FIG. 8, the sleeve element (6) is shown in a perspective view, with the distal end (11) of the sleeve element (6) being particularly visible. In FIG. 9, the sleeve element (6) is shown in another perspective view, the proximal end (12) of the sleeve element (6) being particularly visible. The proximal end (16) of the inner element (7) can also be seen.

Figure 5:
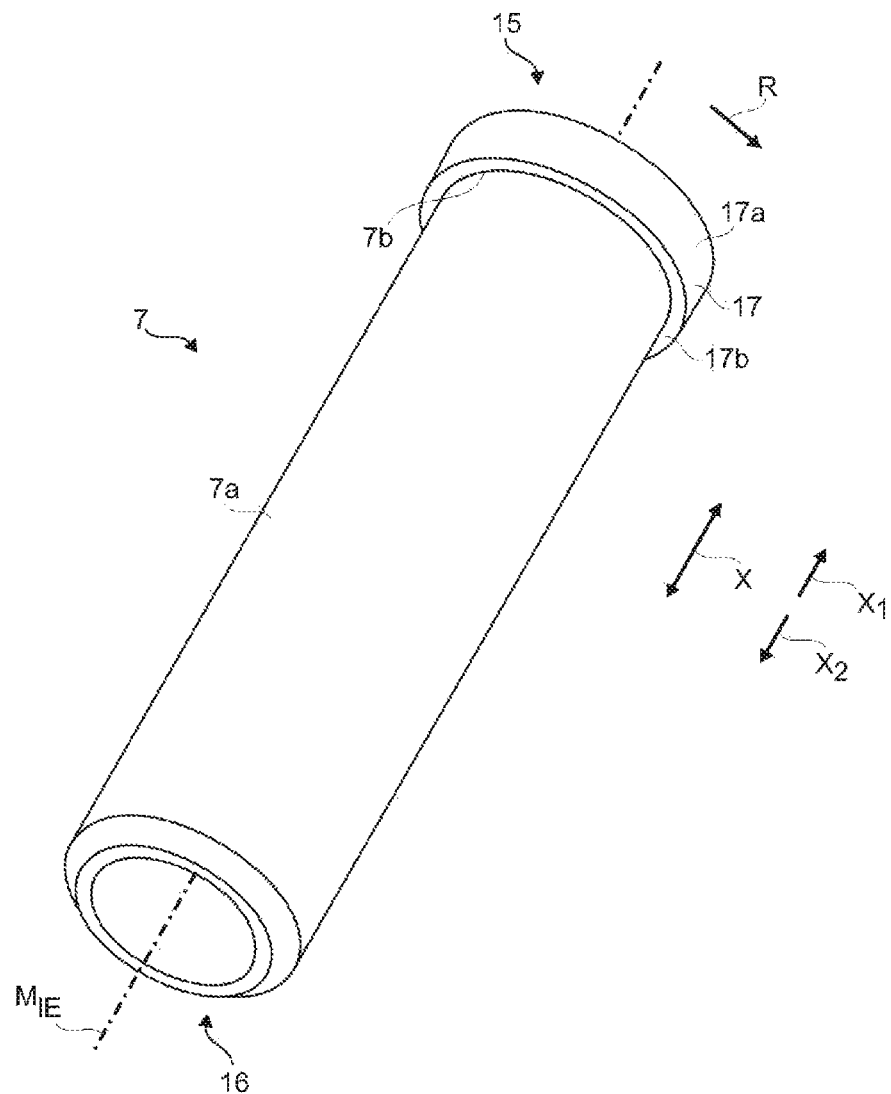
FIG. 5 is a perspective view of the inner element.
Figure 6:
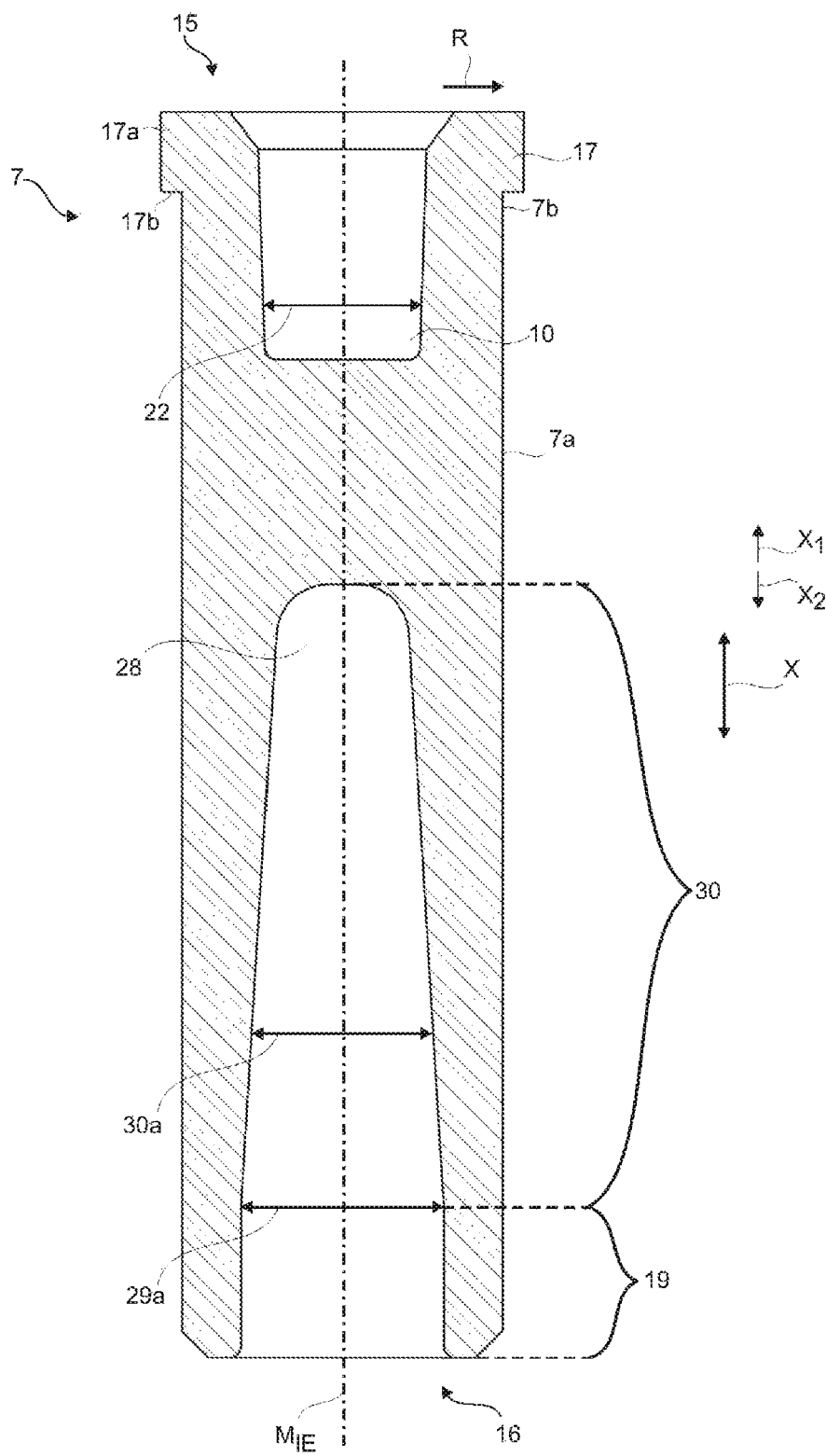
FIG. 6 is a sectional view of the inner element.

The inner element (7) is shown in a sectional view in FIGS. 1 and 6. In FIG. 5, the inner element (7) is shown in perspective. The inner element (7) is configured as a circular cylinder and at its distal end (15) has a cylindrical recess or a blind hole (10). At its proximal end (16), the inner element (7) also has another recess (28) in which the piercing means (5) of the syringe (3) can be arranged.

The other recess (28) has a first portion (29) having a constant inner diameter (29a) in which a distal end piece (3a) of the syringe body (3) can be received. The other recess (28) further has a second portion (30) having an inner diameter (30a) which decreases in an axial direction (X). As a result of the distal end piece (3a) of the syringe body (3) being received in the inner element (7), the piercing means (5) can be closed off in a sterile manner.

At its distal end (15), the inner element (7) also has a flange element (17) extending in a radial direction (R). The flange element (17) is arranged circumferentially on the outer surface (7a) of the inner element (7) and comprises an outer surface (17a) extending in an axial direction (X) and a contact surface (17b) extending in a radial direction (R).

The inner element (7) or the flange element (17) thereof is received in a receiving means (18) of the sleeve element (6). The receiving means (18) is cylindrical and formed integrally with the sleeve element (6). The receiving means (18) is arranged at the distal end (11) of the sleeve element (6) and comprises both a first wall (19), which extends in an axial direction (X) starting from the distal end (11) of the sleeve element (6), and a second wall (20), which extends substantially inwards in a radial direction (R) to a central axis ($M_{IE}$) of the inner element (7). The contact surface (17b) of the inner element (7) rests on the second wall (20). Furthermore, the second wall (20) extends, starting from the first wall (18), inwards towards the central axis ($M_{IE}$) with a gradient in the distal direction ($X_1$).

Figure 2:
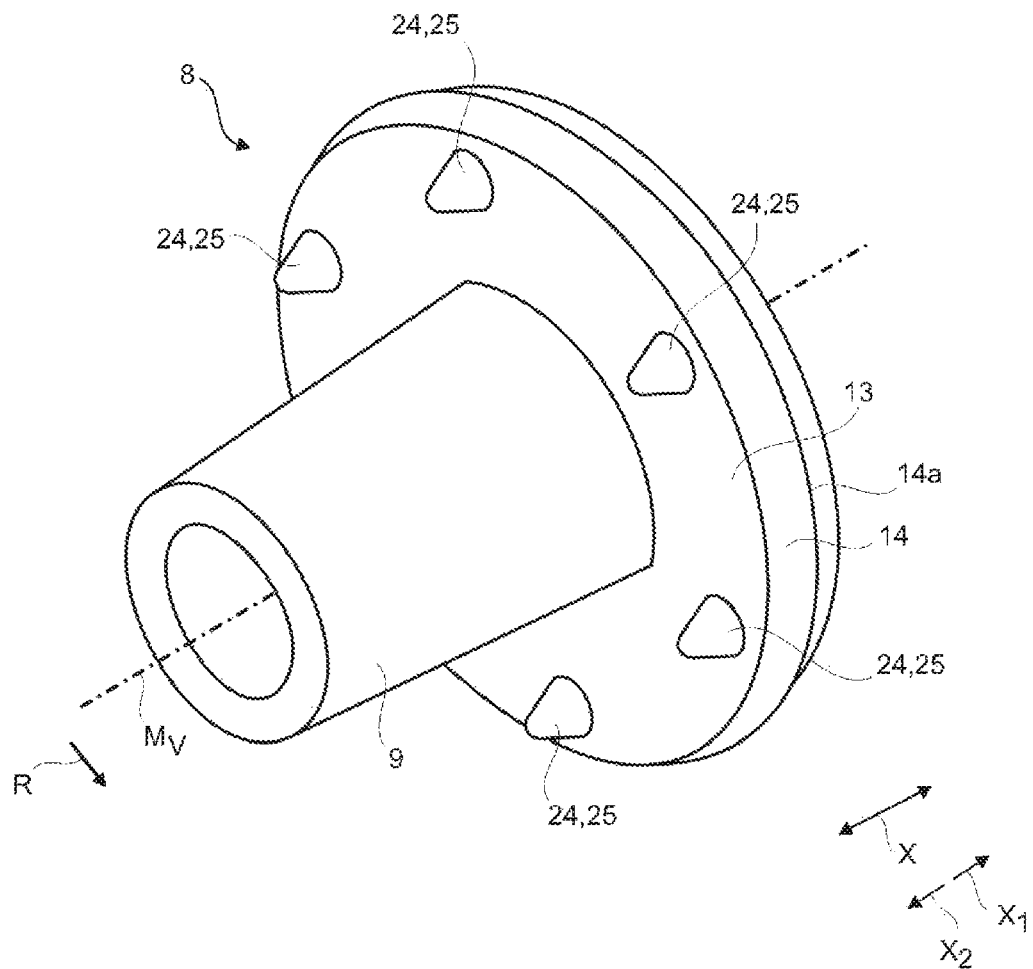
FIG. 2 is a perspective view of a connection element.
Figure 4:
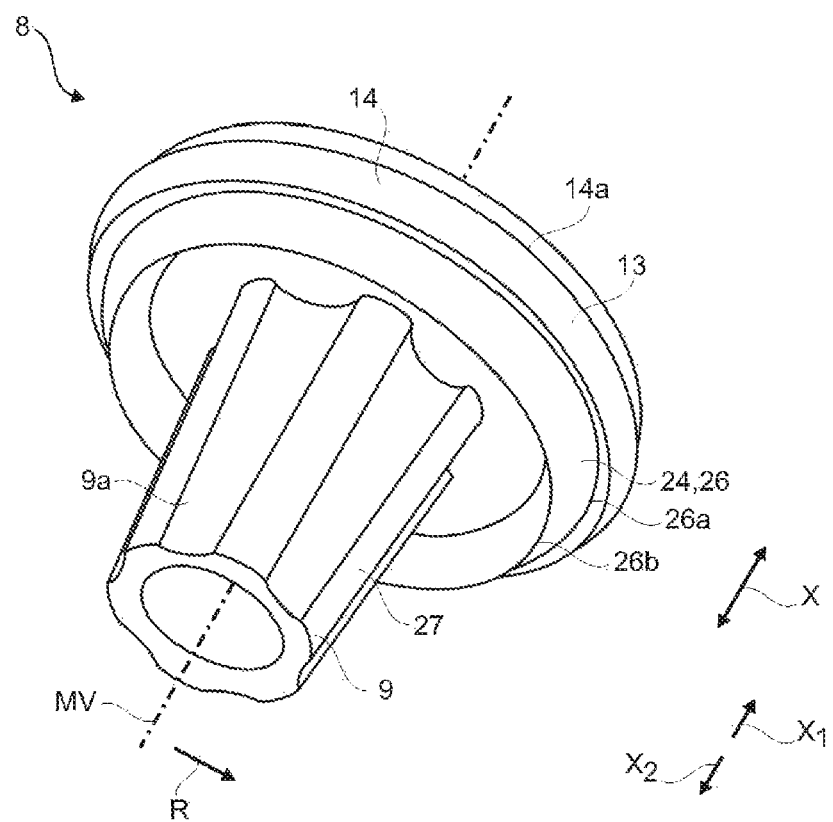
FIG. 4 is a perspective view of another connection element.

The connection element (8) is also shown in FIG. 1 and is arranged at the distal end (11) of the sleeve element (6) and is connected thereto. This connection may be a connection with a force fit and/or an interlocking fit and/or a material-uniting connection. Furthermore, the connection element (8) is connected with a force fit and/or an interlocking fit to the inner element (7). FIGS. 2 and 4 show a connection element (8) according to a first embodiment and FIG. 4 shows a connection element (8) according to another embodiment.

The connection element (8) comprises a circular base element (13) having a central axis ($M_V$). The projection (9) is arranged centrally with regard to the central axis ($M_V$) on the base element (13). The circular base element (13) further has a radial outer surface (14) connected to the sleeve element (6). In particular, a projection (14a) is formed in the radial outer surface (14) and is received in a groove (6a) of the sleeve element. A clip-on connection is thereby achieved between the sleeve element (6) and the connection element (8).

The projection (9) of the connection element (8) is formed conically. An outer diameter (21a) of a first region (21) of the projection (9) is therefore greater than an inner diameter (22) of the recess (10) of the inner element (7). Furthermore, an outer diameter (23a) of a second region (23) of the projection (9) is smaller than an inner diameter (22) of the recess (10). The projection is further formed as a conical hollow cylinder which is closed off at its distal end by the base element (13).

The inner element (7) is resiliently deformed when the projection (9) is received in the recess (10) of the inner element (7). Due to such an interference fit, a resilient force acts between the inner element (7) and the connection element (8) or the sleeve element (6). Due to this deformation, the flange element (17) of the inner element (7) is further pressed in a radial direction (R) onto the receiving means (18). In particular, the outer surface (7a) of the inner element (7) is pressed against the first wall (19) of the receiving means (18). Another connection with a force fit is thus created between the inner element (7) and the sleeve element (6).

A front face (20a) of the second wall (20) is also pressed against a portion (7b) of the inner element (7), which portion lies in a proximal direction ($X_2$) below the flange element (17). On the one hand, another connection with a force fit between the inner element (7) and the sleeve element or the second wall (20) is achieved by this. On the other hand, the flange element is deformed by the conical shape of the projection (9) and the gradient of the second wall (20) in such a way that it approaches or adjoins the second wall. The contact surface (17b) of the flange element (17) thus runs following the deformation in a radial direction outwards with a gradient in a proximal direction. In other words, the receiving means (18) and the inner element interlock in an axial direction (X). A particularly strong connection is therefore created between the inner element (7) and the sleeve element.

The projection (9) on the connection element (8) is arranged centrally with regard to a central axis ($M_H$) of the sleeve element (6). The recess (10) is arranged centrally with regard to a central axis ($M_{IE}$) of the inner element (7). Due to the respective central arrangement and the connection between the connection element (8) and the inner element (7), the inner element (7) can be centred with regard to the sleeve element (6).

Figure 3:
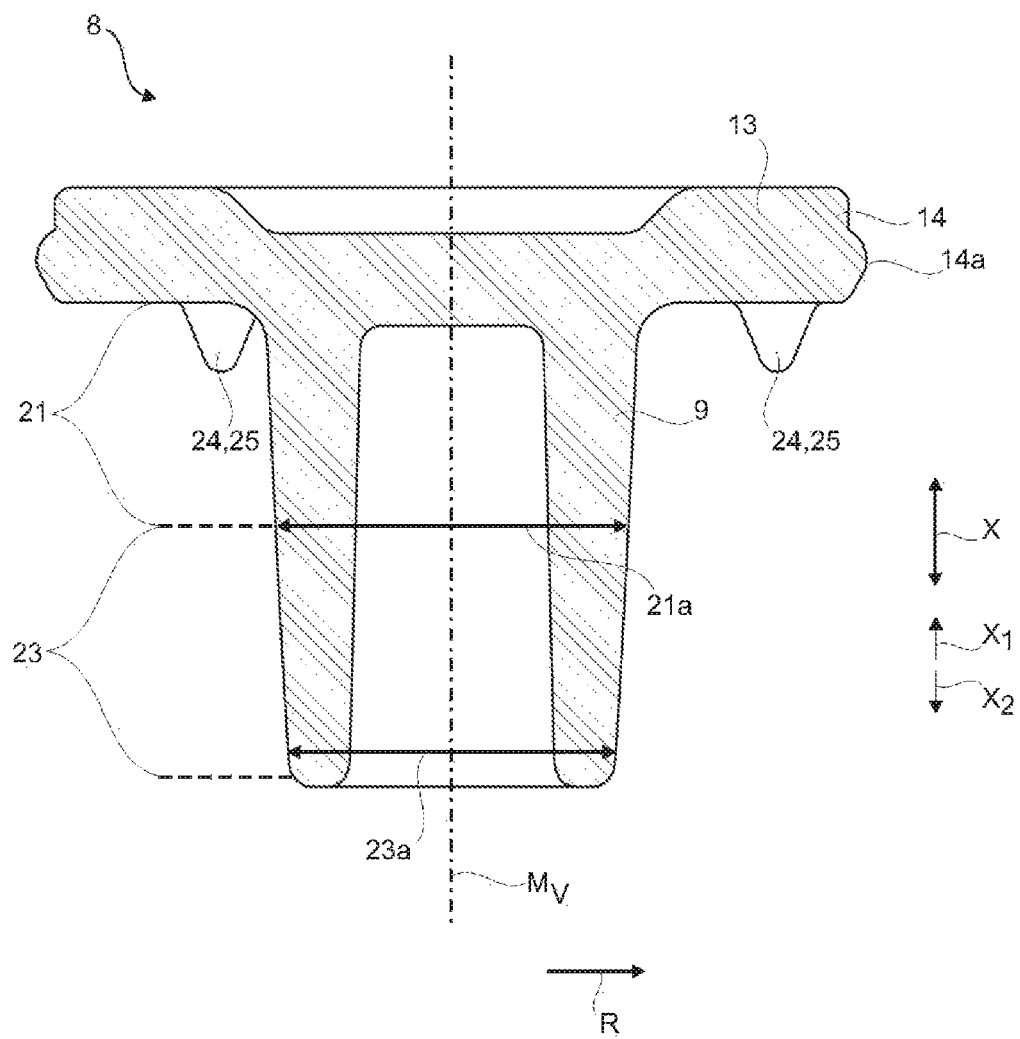
FIG. 3 is a sectional view of the connection element from FIG. 2.

The connection element (8) further has at least one axial tolerance-compensation element (24) on the base element (13) of the connection element (8). According to the embodiment shown in FIGS. 2 and 3, six axial tolerance-compensation elements (24) are arranged on the circular base element (13). These tolerance-compensation elements (24) are arranged in a circular manner around the projection (9) and the central axis ($M_V$). Furthermore, these tolerance-compensation elements (24) are configured as cone-shaped projections (25) or mandrels which extend in a proximal direction ($X_2$) towards the inner element (7) and contact and deform the inner element (7) or even penetrate it.

According to another embodiment, the axial tolerance-compensation element (24) is configured as an annular element (26) surrounding the projection (9), wherein the annular element (26) tapers in an axial direction (X) towards the inner element (7) and in a proximal direction ($X_2$). The annular element (26) thus has a broad base area (26a) which is arranged on the circular base element (13). In addition, the annular element (26) has a narrow edge (26b) which lies centrally above the base area (26a) and deforms/compresses or penetrates the inner element (7).

In the embodiment according to FIG. 4, the projection (9) comprises an outer surface (9a) on which ribs are arranged. The ribs (27) run in an axial direction (X) and extend outwards in a radial direction (R). These ribs (27) can deform/compress or penetrate the resilient material of the inner element (7). A more stable connection can thus be achieved between the inner element (7) and the connection element (8).

All the features disclosed in the application documents are claimed as essential to the invention if they are novel individually or in combination compared with the prior art.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

When a group of materials, compositions, components or compounds is disclosed herein, it is understood that all individual members of those groups and all subgroups thereof are disclosed separately. Every formulation or combination of components described or exemplified herein can be used to practice the invention, unless otherwise stated. Whenever a range is given in the specification, for example, a composition range, all intermediate ranges and subranges, as well as all individual values included in the ranges given are intended to be included in the disclosure. Additionally, the end points in a given range are to be included within the range. In the disclosure and the claims, "and/or" means additionally or alternatively. Moreover, any use of a term in the singular also encompasses plural forms.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements.

One of ordinary skill in the art will appreciate that starting materials, device elements, analytical methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed.

The invention illustratively described herein suitably may be practiced in the absence of any element or elements, limitation or limitations which is not specifically disclosed herein. Headings are used herein for convenience only.

LIST OF REFERENCE SIGNS

1 Device
2 Syringe
3 Syringe body
3a Distal end piece of the syringe body
3b Distal end region of the syringe body
4 Distal end of the syringe body
5 Piercing means
6 Sleeve element
6a Groove in sleeve element
7 Inner element
7a Outer surface of the inner element
7b Portion of the inner element
8 Connection element
9 Projection on the connection element
9a Outer surface of the projection
10 Recess of the inner element
11 Distal end of the sleeve element
12 Proximal end of the sleeve element
13 Circular base element
14 Radial outer surface
14a Projection on the radial outer surface
15 Distal end of the inner element
16 Proximal end of the inner element
17 Flange element
17a Outer surface of the flange element
17b Contact surface of the flange element
18 Receiving means of the sleeve element
19 First wall of the receiving means
20 Second wall of the receiving means
21 First region of the projection
21a Outer diameter of the first region
22 Inner diameter of the recess of the inner element
23 Second region of the projection
23a Outer diameter of the second region
24 Axial tolerance-compensation element
25 Cone-shaped projections
26 Circumferential ring
26a Base area of the ring
27 Ribs
28 Other recess of the inner element
29 First portion of the other recess
29a Inner diameter of the first portion of the other recess
30 Second portion of the other recess
30a Inner diameter of the second portion of the other recess
$M_H$ Central axis of the sleeve element
$M_{IE}$ Central axis of the inner element
$M_V$ Central axis of the connection element
R Radial direction
X Axial direction
$X_1$ Distal direction
$X_2$ Proximal direction

The invention claimed is:

1. A piercing means protective device for a syringe comprising a syringe body and a piercing means arranged at the distal end of the syringe body, comprising a dimensionally stable sleeve element, which extends along an axial direction and at least partially encloses an inner element extending along an axial direction, wherein the inner element consists of a resilient material and at least partially encloses the piercing means, wherein a connection element connected to the sleeve element in an interlocking fit connection has at least one projection extending in an axial direction, which projection is received at least in portions in a recess of the inner element, so that a connection exists with a force fit and/or an interlocking fit between the sleeve element and the inner element, wherein the projection is arranged centrally on the connection element with respect to a central axis of the sleeve element, wherein the inner element has a distal end and a flange element at the distal end extending in a radial direction, where said flange element is received in a receiving means of the sleeve element, wherein the receiving means is arranged on the distal end of the sleeve element and has a first wall which extends in an axial direction starting from the distal most end of the sleeve element, and a second wall which extends substantially in a radial direction and wherein the first wall is arranged at a distance in a radial direction to a portion of the sleeve element.

2. The piercing means protective device according to claim 1, wherein the sleeve element is formed substantially as a circular hollow cylinder and has a distal and a proximal end, wherein the connection element is arranged at the distal end of the sleeve element.

3. The piercing means protective device according to claim 1, wherein the connection element has a circular base element on which the projection is arranged, wherein the circular base element has a radial outer surface which is connected to the sleeve element.

4. The piercing means protective device according to claim 1, wherein the recess is arranged centrally with respect to a central axis of the inner element, wherein due to the respective central arrangement and the connection between the connection element and the inner element, the inner element is be centred with respect to the sleeve element.

5. The piercing means protective device according to claim 1, wherein the projection of the connection element is formed conically, wherein an outer diameter of a first region of the projection is greater than an inner diameter of the recess of the inner element, wherein the inner element is resiliently deformed when the projection is received in the recess of the inner element, wherein the flange element of the inner element is pressed by this deformation in a radial direction onto the receiving means.

6. The piercing means protective device according to claim 3, wherein arranged on the base element of the connection element is at least one axial tolerance-compensation element, which extends in an axial direction towards the inner element and contacts the inner element.

7. The piercing means protective device according to claim 6, wherein arranged on the base element of the connection element are at least two axial tolerance-compensation elements, which are configured as cone-shaped projections, wherein the at least two axial tolerance-compensation elements are arranged in a circular manner around the projection.

8. The piercing means protective device according to claim 6, wherein the axial tolerance-compensation element is configured as an annular element surrounding the projection, wherein the annular element tapers in an axial direction towards the inner element.

9. The piercing means protective device according to claim 1, wherein the projection comprises an outer surface on which ribs running in an axial direction are arranged.

10. A prefilled syringe comprising a syringe body and a piercing means arranged at a distal end of the syringe body, and further comprising a piercing means protective device comprising a dimensionally stable sleeve element, which extends along an axial direction and at least partially encloses an inner element extending along an axial direction,
   wherein the inner element consists of a resilient material and at least partially encloses the piercing means, wherein a connection element connected to the sleeve element in an interlocking fit connection has at least one projection extending in an axial direction, wherein the projection is received at least in portions in a recess of the inner element, so that a connection exists with a force fit and/or an interlocking fit between the sleeve element and the inner element,
   wherein the projection is arranged centrally on the connection element with respect to a central axis of the sleeve element, wherein the inner element has a distal end and a flange element at the distal end extending in a radial direction, where said flange element is received in a receiving means of the sleeve element, wherein the receiving means is arranged on the distal most end of the sleeve element and has a first wall which extends in an axial direction starting from the distal end of the sleeve element, and a second wall which extends substantially in a radial direction and wherein the first wall is arranged at a distance in a radial direction to a portion of the sleeve element.

11. The piercing means protective device according to claim 2, wherein the inner element has at its distal end a flange element extending in a radial direction, where said element is received in a receiving means of the sleeve element, wherein the receiving means is arranged on the distal end of the sleeve element and has a first wall which extends in an axial direction starting from the distal end of the sleeve element, and a second wall which extends substantially in a radial direction.

12. The piercing means protective device according to claim 3, wherein the projection of the connection element is formed conically, wherein an outer diameter of a first region of the projection is greater than an inner diameter of the recess of the inner element, wherein the inner element is resiliently deformed when the projection is received in the recess of the inner element, wherein the flange element of the inner element is pressed by this deformation in a radial direction onto the receiving means.

13. The piercing means protective device according to claim 4, wherein the projection of the connection element is formed conically, wherein an outer diameter of a first region of the projection is greater than an inner diameter of the recess of the inner element, wherein the inner element is resiliently deformed when the projection is received in the recess of the inner element, wherein the flange element of the inner element is pressed by this deformation in a radial direction onto the receiving means.

14. The piercing means protective device according to claim 4, wherein arranged on the base element of the connection element is at least one axial tolerance-compensation element, which extends in an axial direction towards the inner element and contacts the inner element.

15. The piercing means protective device according to claim 5, wherein arranged on the base element of the connection element is at least one axial tolerance-compensation element, which extends in an axial direction towards the inner element and contacts the inner element.

* * * * *